(12) United States Patent
Kim et al.

(10) Patent No.: US 9,408,975 B2
(45) Date of Patent: Aug. 9, 2016

(54) APPARATUS FOR OPERATING SYRINGE PISTON

(71) Applicants: Seok-Jung Kim, Uijeongbu-Si (KR); Cheong-Ho Chang, Seoul (KR); Jae-Deog Jang, Seoul (KR); Hyun-Shin Park, Seoul (KR); Sae-Bom Lee, Seoul (KR); Kyoung-Phil Byun, Goyang-Si (KR)

(72) Inventors: Seok-Jung Kim, Uijeongbu-Si (KR); Cheong-Ho Chang, Seoul (KR); Jae-Deog Jang, Seoul (KR); Hyun-Shin Park, Seoul (KR); Sae-Bom Lee, Seoul (KR); Kyoung-Phil Byun, Goyang-Si (KR)

(*) Notice: Subject to any disclaimer, the term of this patent is extended or adjusted under 35 U.S.C. 154(b) by 348 days.

(21) Appl. No.: 14/019,657

(22) Filed: Sep. 6, 2013

(65) Prior Publication Data
US 2015/0073351 A1 Mar. 12, 2015

(51) Int. Cl.
*A61M 5/31* (2006.01)
*A61M 5/315* (2006.01)
*A61M 5/48* (2006.01)
*A61M 5/20* (2006.01)

(52) U.S. Cl.
CPC .............. *A61M 5/31511* (2013.01); *A61M 5/20* (2013.01); *A61M 5/31* (2013.01); *A61M 5/31565* (2013.01); *A61M 5/484* (2013.01); *A61M 2005/2026* (2013.01)

(58) Field of Classification Search
CPC . A61M 2005/2026; A61M 5/20; A61M 5/31; A61M 5/31511; A61M 5/31565; A61M 5/484
See application file for complete search history.

(56) References Cited

U.S. PATENT DOCUMENTS

| | | | | |
|---|---|---|---|---|
| 2,859,751 A | * | 11/1958 | Stroop | A61M 5/24 604/227 |
| 2003/0109884 A1 | * | 6/2003 | Tague | A61B 17/8833 606/94 |

* cited by examiner

*Primary Examiner* — Imani Hayman
(74) *Attorney, Agent, or Firm* — G W i P S

(57) ABSTRACT

An apparatus for operating a syringe has developed comprising: an upper semi-cylindrical tube section, semi-circular shaped locking groove and lower semi-cylindrical tube section. The upper semi-cylindrical tube section is integrally formed an upper head part with a threaded hole for axial movement. The lower semi-cylindrical tube section forms a top portion, intermediate portion and end portion. A diameter (Dc) at the intermediate portion larger than the diameter (Dtip) at end portion is gradually reduced from intermediate to end portion. The length of the tapered portion is same as that portion of the constant diameter. A tip portion has formed an opened semi-circular shape to simply overlap the syringe over the cartridge for easily snapping-in and out. The syringe piston moves downward with no reverse action when the piston press-unit is rotated, thus it is possible to inject the precise amount of medicine to a patient with constant pressure.

3 Claims, 7 Drawing Sheets

APPARATUS FOR OPERATING SYRINGE PISTON

This application is a Continuation in Part of patent application Ser. No. 12/226,316, which is filed Oct. 15, 2008 and claims the priority of Korean Patent Application No. 10-2006-0036206, which is filed Apr. 21, 2006 and entire disclosure of which is herewith incorporated by reference.

BACKGROUND OF THE INVENTION

1. Field of the Invention

The present invention relates to an apparatus for operating a syringe piston. More particularly, it is comprised of a syringe mounting section for holding a medicine filled syringe and a piston press unit for operating a syringe piston without reverse action while the piston is depressing, so that the medicine contained in the syringe can be injected into a patient's body with constant pressure, ensuring that an accurate amount of medicine is delivered.

2. Related Prior Art

As generally known in the art, a syringe is a device for injecting a liquid medicine into a tissue of a living body. The syringe mainly includes a needle inserted into the tissue of the living body, a glass cylinder containing the liquid medicine, and a piston for applying pressure to the liquid medicine. Recently, the disposable plastic syringes have extensively used in order to avoid the diseases transmitting through the serum infection.

Meanwhile, a medical treatment employing medical cement has been proposed to cure lesions, such as the fracture, amputation or necrosis of a bone. According to the above medical treatment employing the medical cement, an incision is made so that the surgeon can see the injured bone with the naked eye, and then the medical cement is injected into the lesion part. Otherwise, the surgeon checks the lesion part by observing the bone using an imaging device, and then injects the medical cement into the tissue of the patient using the syringe.

However, the conventional syringe is rarely used for this type of procedure due to the following reason: when the medical cement is injected into the tissue of the patient, a relatively great pressure must be applied to the piston due to the physical properties of the medical cement. However, it is very difficult to manually apply a constant pressure to the piston, thus it is also very difficult to inject a precise amount of medical cement into the tissue of the patient.

SUMMARY OF THE INVENTION

Accordingly, the present invention has been made to solve the above-mentioned problems occurring in the prior art. A first object of the present invention is to provide an apparatus for operating a syringe piston, which includes a syringe mounting section for securely mounting a syringe and a piston press unit for pressing the syringe piston with a constant pressure.

A second object of the present invention is to provide an apparatus for operating a syringe piston, in which a syringe filled with medical cement is attached to a syringe mounting section and the syringe piston is moved downward without any reverse motion when a user rotates a threaded rod of the piston press unit, the medical cement contained in the syringe will be extruded from the syringe tube with a constant pressure, so that a predetermined amount of medical cement can be precisely injected into a human body.

A third object of the present invention is to provide an apparatus for operating a syringe piston, which can significantly improve the medical technique.

A fourth object of the present invention is to provide an apparatus for operating a syringe piston, which can significantly improve the quality and reliability of procedures, thereby providing consumers with high satisfaction and a good impression.

In order to accomplish the above objects, according to the present invention, there is provided an apparatus for operating a syringe piston, the apparatus comprising: a syringe mounting section for fixedly mounting a syringe, in which a screw hole is formed at an upper head part of the syringe mounting section; and a piston press unit having a threaded rod, which is threaded into the screw hole so that the syringe piston press unit can move up and down along the screw hole, wherein the piston press unit presses a syringe piston with a constant pressure such that a predetermined amount of contents is precisely injected into a human body from the syringe.

The apparatus for operating a syringe piston is comprised of: a syringe mounting device (10) composed of an upper semi-cylindrical tube section, a semi-circular shaped locking groove (14) and a lower semi-cylindrical tube section (13); the upper semi-cylindrical tube section of the syringe mounting device integrally formed with an upper head part (11) with a threaded hole (12) for movement of the syringe piston therein; the lower semi-cylindrical tube section (13) of the syringe mounting device composed of a top portion, an intermediate portion and an end portion, and the end portion is the opposite side of the upper head part (11) of the upper semi-cylindrical tube section; an inner diameter (Dc) at the intermediate portion is larger than the inner diameter (Dtip) at the end portion of the lower semi-cylindrical tube section (13), so that the inner diameter (Dc) of the lower semi-cylindrical tube section is gradually reduced from the intermediate portion to the end portion of the lower semi-cylindrical tube section to form a smooth taper. Thus, a length of the tapered portion from the intermediate portion to the end portion is almost same as the length of the constant diameter (Dc) portion from the intermediate portion to the top portion. The syringe is press-fitted into the syringe mounting device, so that the smaller diameter portion (Dtip) of the lower semi-cylindrical tube section creates a frictional fit to secure the syringe so that it prevents the syringe easily separating from the lower semi-cylindrical tube section. The semi-circular shaped locking groove (14) disposed between the upper semi-cylindrical tube section (10) and the lower semi-cylindrical tube section (13) is for receiving a flange of the syringe fixedly, so that the axial movement of the syringe is prevented. Further, a piston press unit (20) with a threaded rod (24) is screw-coupled to the threaded hole (12), so that the piston press unit (20) is movable along with the threaded hole (12), while the syringe piston is depressed with a constant pressure for injecting a precise amount of medicine into a patient body.

The piston press unit (20) is comprised of a handle (21) with an anti-slip knob section (22) formed at an outer peripheral surface of handle (21) for easily turning the handle. The handle (21) comprises a polygonal section (23) formed at a lower end portion thereof. The figures are marked on the polygonal section (23) to accurately calibrate an amount of the injecting medicine. The inner diameter (Dc) of the lower semi-cylindrical tube section is gradually reduced from the intermediate portion (13) to the end portion (15) of the lower semi-cylindrical tube section.

DETAILED DESCRIPTION OF THE PREFERRED EMBODIMENTS

Hereinafter, an apparatus for operating a syringe piston according to a preferred embodiment of the present invention will be described with reference to FIGS. 1 to 7.

In the following description of the present invention, the explanations of the known functions and configurations, which are incorporated with the subject matter of the present invention, will be omitted.

In addition, the terms used in the following description of the present invention are prepared in view of functions thereof, so they will be changed depending on the intention of manufacturers or custom. Thus, definition of the terms must be determined based on the whole content of the specification.

The present invention provides an apparatus for operating a syringe, which is comprised of a syringe mounting section (10) for securely holding a syringe (30) and a piston press unit (20) for operating a syringe piston (31) with a constant pressure. The syringe (30) filled with medical cement is placed into the syringe mounting section (10) for operating the syringe piston (31) downward without any reverse motion. When a screw of the piston press unit (20) is rotated, the medicine contained in the syringe (30) can be injected into the patient from the syringe (30) with a constant pressure. So, a precise amount of medicine can be injected into a patient's body. Hereinafter, the structure of the present invention will be described in more detail.

Figure 1:
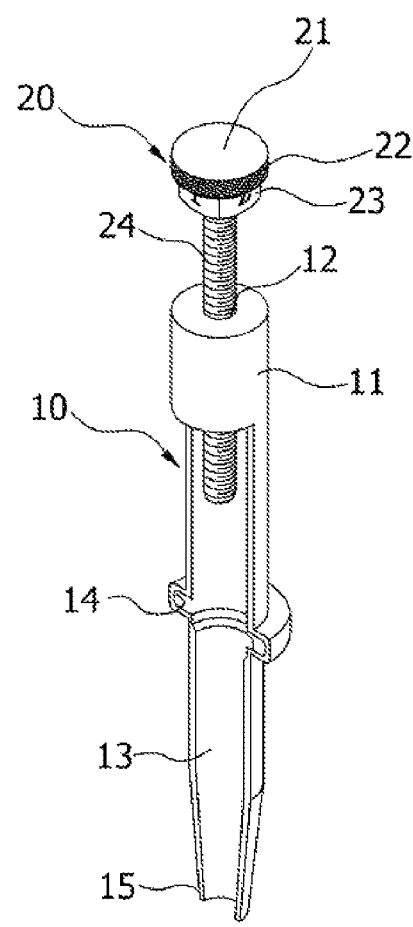
FIG. 1 is a perspective view illustrating an apparatus for operating a syringe piston according to the present invention.
Figure 2:
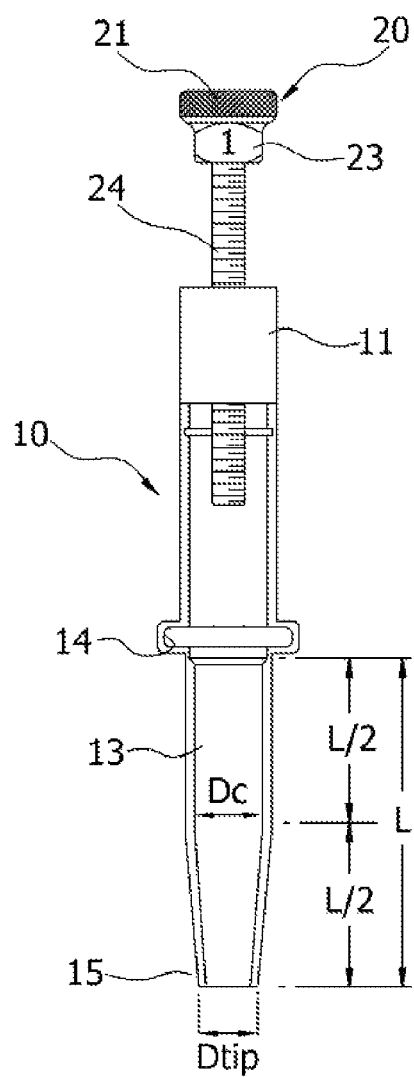
FIG. 2 is a front view illustrating an apparatus for operating a syringe piston according to the present invention.
Figure 3:
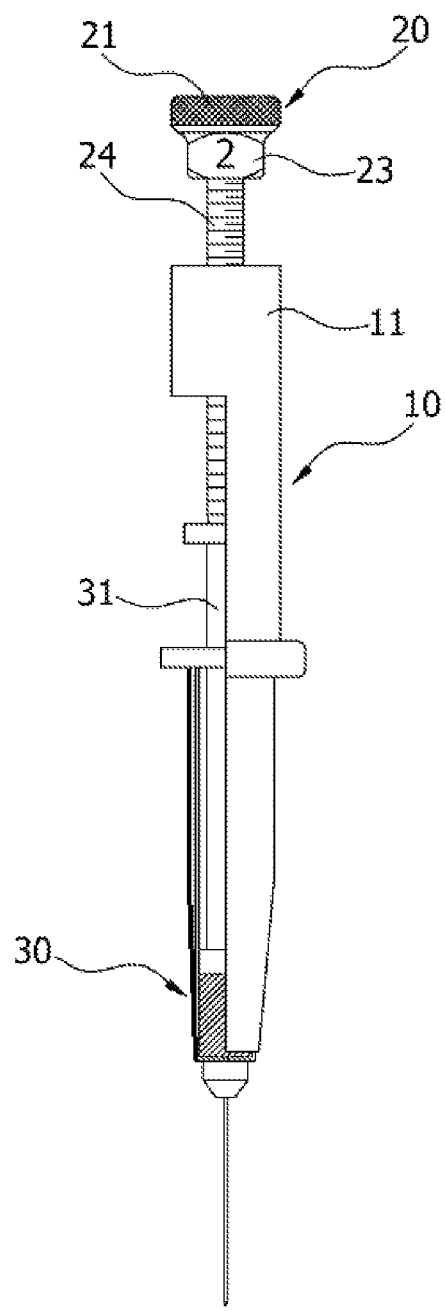
FIG. 3 is a side view illustrating an apparatus for operating a syringe piston according to the present invention.

The syringe mounting section (10) is integrally formed with an upper portion of the semi-cylindrical tube, a semi-circular shaped locking groove (14), and a lower portion of the semi-cylindrical tube (13) for detachably mounting the syringe (30) while allowing an operator to see the inside of the syringe mounting section (10) from the exterior. The upper semi-cylindrical tube section of the syringe mounting device integrally formed with an upper head part (11) with a threaded hole (12) for the movement of the syringe piston therein. The lower semi-cylindrical tube section (13) of the syringe mounting device composed of a top portion (14), an intermediate portion and an end portion (15), and the end portion (15) is the opposite side of the upper head part (11) of the upper semi-cylindrical tube section. The inner diameter "Dc" of an intermediate portion of the semi-cylindrical tube (13) is larger than the diameter "Dtip" of a lower tip portion of the semi-cylindrical tube (13), so the syringe (30) is press-fitted into the semi-cylindrical tube (13) while generating a "click" sound, so that the syringe (30) is prevented from easily falling off of the semi-cylindrical tube (13). As shown in FIG. 2, the inner diameter (Dc) of the lower semi-cylindrical tube section is gradually reduced from the intermediate portion to the end portion (15) of the lower semi-cylindrical tube section to form a smooth taper. Thus, a length of the tapered portion (L/2) from the intermediate portion to the end portion is approximately same as the length of the constant diameter (Dc) from the intermediate portion to the top portion (14).

Because the syringe is press-fitted into the syringe mounting device, the smaller diameter portion (Dtip) of the lower semi-cylindrical tube section creates a frictional fit to secure the syringe, so that it prevents the syringe easily separating from the lower semi-cylindrical tube section, In addition, the syringe mounting section (10) is formed with a semi-circular shaped locking groove (14), where the flange of the syringe is fixedly inserted. The semi-circular shaped locking groove (14), which is disposed between the upper semi-cylindrical tube section (10) and the lower semi-cylindrical tube section (13) is for receiving a flange of the syringe fixedly, so that the axial movement of the syringe is prevented. A piston press unit (20) has a threaded rod (24), which is screw-coupled to the threaded hole (12), so that the piston press unit (20) is movable along the threaded hole (12), while the syringe piston is depressed with a constant pressure for injecting a precise amount of medicine to a patient body.

A handle (21) with an anti-slip knob section (22) is provided at an upper end portion of the piston press unit (20). The handle (21) is provided at an outer peripheral surface thereof with a knurled section (22) so as to allow a user to easily rotate the handle (21).

In addition, a polygonal mark section (23) is provided at a lower end portion of the handle (21). The figures, characters or symbols are formed in the polygonal mark section (23) so as to allow the user to rotate the piston press unit (20) corresponding to an amount of medical cement to be discharged from the syringe (30). Therefore, the apparatus for operating a syringe piston of the present invention is accurately calibrated to inject the amount of the medicine to the patient.

Particularly, according to the present invention, the pitch of a threaded rod (24) and a screw hole (12) is established such that 100 ml of contents can be discharged from the syringe (30) as the user rotates the piston press unit (20) one time.

Hereinafter, the operation and effect of the present invention having the above structure will be described.

First, the user fills the syringe (30) with contents. At this time, the contents refer to a liquid medicine, which is injected into a tissue of a living body. According to the present invention, the contents preferably include medical cement used for curing lesions, such as the fracture, amputation or necrosis of a bone.

Figure 4:
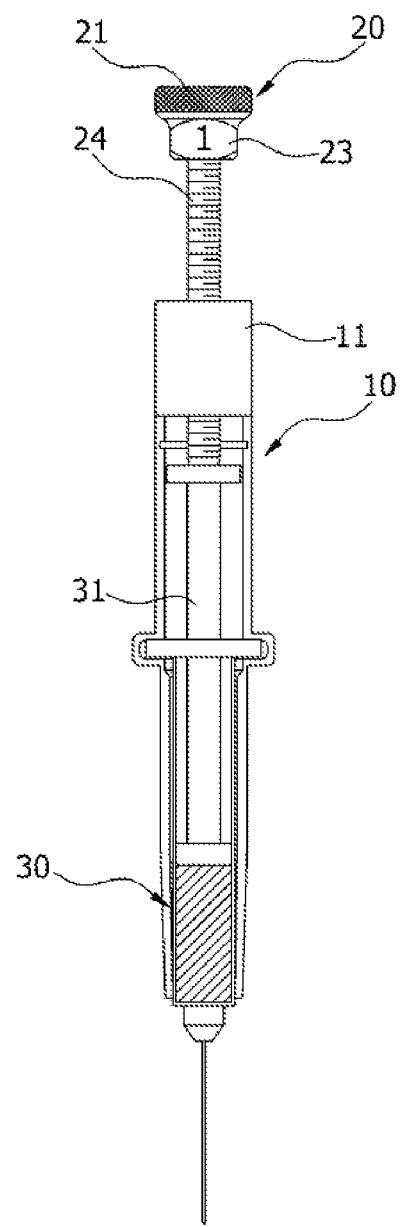
FIG. 4 is a view illustrating an apparatus for operating a syringe piston according to the present invention, in which a piston press unit has not yet moved downward.
Figure 5:
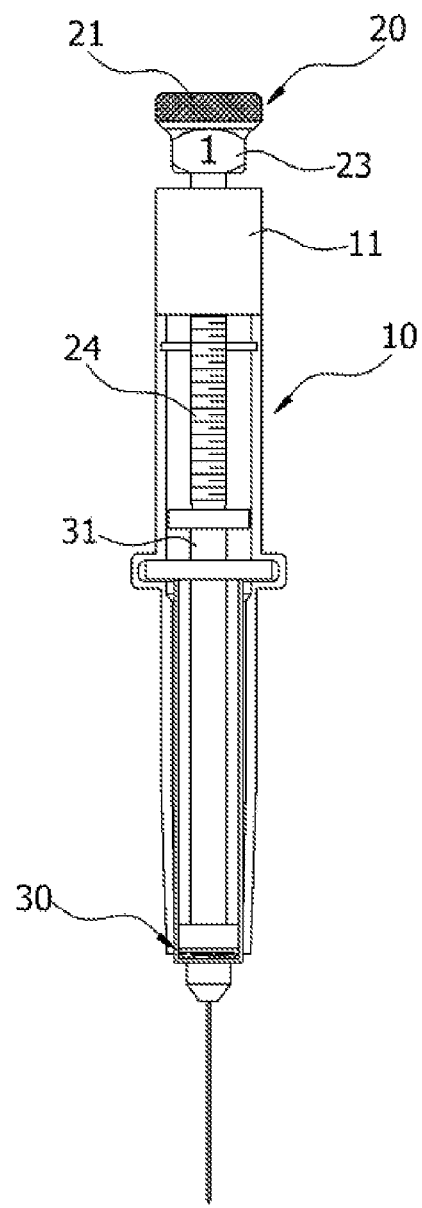
FIG. 5 is a view illustrating an apparatus for operating a syringe piston according to the present invention, in which a piston press unit moves downward while pushing a syringe piston in the downward direction.

As shown in FIGS. 4 and 5, the syringe (30) filled with the medical cement is attached to the syringe mounting section (10). Since the syringe mounting section (10) is formed as a semi-cylindrical tube (13), about half of the syringe (30) is accommodated in the syringe mounting section (10). In addition, as shown in FIG. 2, since the diameter "Dc" of the intermediate portion of the semi-cylindrical tube (13) is larger than the diameter "Dtip" of the lower tip portion (15) of the semi-cylindrical tube, the syringe (30) is press-fitted into the semi-cylindrical tube (13) while generating a "click" sound, so that the syringe (30) can be prevented from being easily separated from the semi-cylindrical tube (13).

Figure 7A:
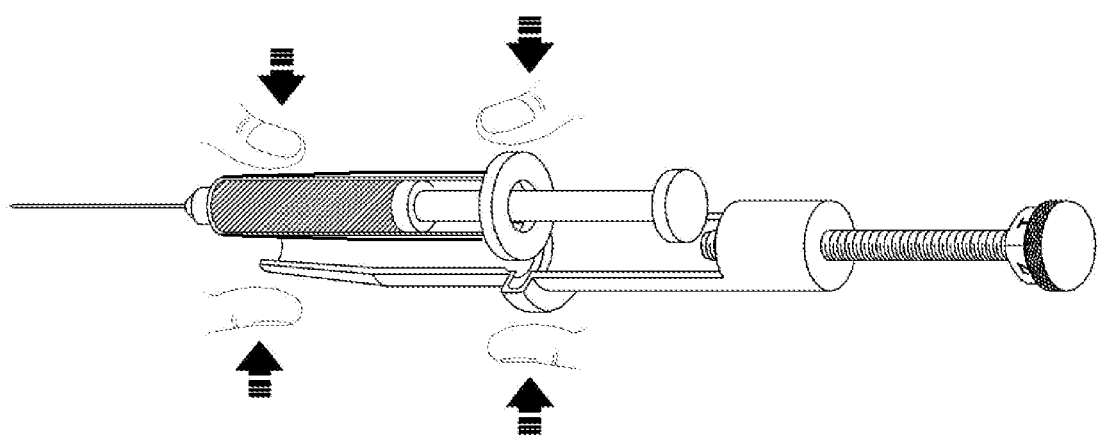
FIG. 7A is the perspective views showing a syringe filled medicine is snapping into the syringe mounting device of the present invention.
Figure 7B:
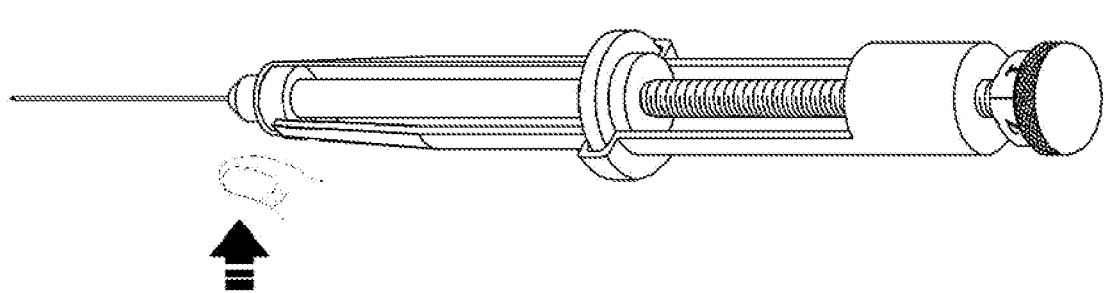
FIG. 7B is the perspective views showing the empty syringe is snapping out from the syringe mounting device of the present invention.

As shown in FIG. 7A, the medicine filled syringe is simply overlapped above the syringe mounting device. Then, the syringe overlapped above the syringe mounting device is depressed to snap-in by using both thumbs and first fingers until it sounds "click". The tip (15) of the lower semi-cylindrical tube (13) is formed an opened semi-circular shape for easily snapping in.

When the syringe (30) is press-fitted into the semi-cylindrical tube (13), an upper protrusion of the syringe (30) is firmly fitted into the locking groove (14), simultaneously. Thus, the syringe (30) can be prevented sliding along the semi-cylindrical tube (13), when the syringe piston (31) is pressed for injection with a constant pressure.

After the syringe (30) filled with the medical cement has been press-fitted into the syringe mounting section (10), the piston press unit (20) is coupled to the syringe mounting section (10).

That is, the threaded rod (24) is threaded into the screw hole (12) formed at the center portion of an upper head part (11) of the syringe mounting section (10). At this time, as mentioned above, the pitch of the threaded rod (24) is predetermined such that 100 ml of contents can be discharged from the syringe (30) as the user rotates the piston press unit (20) one time.

Figure 6:
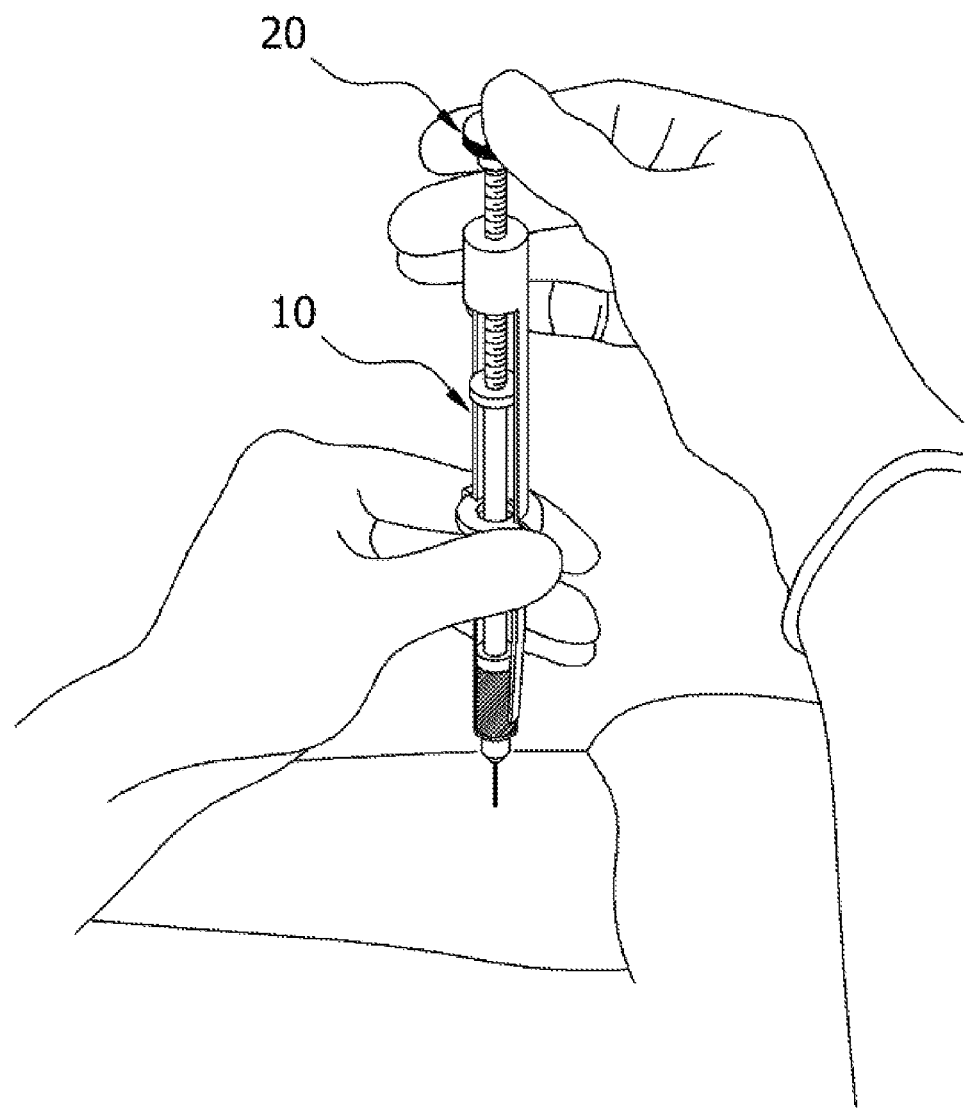
FIG. 6 is a perspective view illustrating an operational state of an apparatus for operating a syringe piston according to the present invention.

In detail, if the user rotates the piston press unit (20), a lower tip portion of the piston press unit (20) makes contact with an upper end portion of the syringe piston (31) as shown in FIGS. 4 and 6. In this state, if the user further rotates the piston press unit (20), the piston press unit (20) moves down together with the syringe piston (31) so that the contents (medical cement) of the syringe (30) are extruded from the syringe (30). Thus, the medical cement can be injected into a tissue of a patient. After completing the injection, the empty syringe is removed from the syringe mounting device by simply pushing up with the thumb.

According to the present invention, the syringe (30) filled with medical cement is mounted into the syringe mounting section (10) and the syringe piston (31) is moved downward with no reverse action when the user rotates the piston press unit (20) having the threaded rod, so that the medical cement contained in the syringe (30) can be extruded from the syringe (30) with a constant pressure to precisely inject a predetermined amount of medical cement to a human body. Thus, the present invention can significantly improve the medical technique.

Meanwhile, since the handle (21) is provided at the outer peripheral surface thereof with the knurled section (22), the user can easily rotate the handle (21) without slipping from the handle (21).

In addition, since the polygonal mark section (23) is provided at the lower end portion of the handle (21), the user can properly rotate the piston press unit (20) corresponding to the amount of medical cement to be discharged. That is, the user can adjust the rotation degree of the piston press unit (20) based on figures marked on the polygonal mark section (23). For instance, if it is necessary to inject 50 ml of contents into the tissue of the patient, the user simply rotates the piston press unit (20) by an angle of 180 degrees (that is, the user rotates the piston press unit (20) until a figure "3" is located in the front of the polygonal mark section (23).

The apparatus for operating the syringe piston according to the present invention can be mainly used for medical purposes. Of course, the apparatus of the present invention can also be used at home and in industrial fields.

As described above, the present invention provides the apparatus for operating the syringe piston, which includes the syringe mounting section for securely mounting the syringe and the piston press unit for pressing the syringe piston with a constant pressure. In particular, the syringe filled with medical cement is inserted to the syringe mounting section and the syringe piston is moved downward with no reverse movement when the user rotates the piston press unit having the threaded rod, so medical cement contained in the syringe can be extruded from the syringe with a constant pressure for precisely injecting a predetermined amount of medical cement into a human body. As a result, the apparatus for operating the syringe piston according to the present invention can significantly improve quality and reliability of procedures, thereby providing consumers with high satisfaction and a good impression.

Meanwhile, the structure of the present invention can be variously modified and changed.

In addition, the present invention is not limited to the above embodiment, and those skilled in the art will appreciate that various modifications, additions and substitutions are possible, without departing from the scope and spirit of the invention as disclosed in the accompanying claims.

What is claimed is:

1. An apparatus for operating a syringe piston, the apparatus comprising:
   a syringe mounting device (10) comprising an upper semi-cylindrical tube section, a semi-circular shaped locking groove (14) and a lower semi-cylindrical tube section (13),
   said upper semi-cylindrical tube section of the syringe mounting device integrally formed with an upper head part (11) with a threaded hole (12) for axial movement of the syringe piston therein,
   wherein said lower semi-cylindrical tube section (13) of the syringe mounting device comprising a top portion, an intermediate portion and an end portion (15), and the end portion is the opposite side of the upper head part (11) of the upper semi-cylindrical tube section,
   an inner diameter (Dc) at the intermediate portion is larger than the inner diameter (Dtip) at the end portion of the lower semi-cylindrical tube section (13), so that the inner diameter (Dc) of the lower semi-cylindrical tube section is gradually reduced from the intermediate portion to the end portion of the lower semi-cylindrical tube section to form a smooth taper, wherein a length of the tapered portion from the intermediate portion to the end portion is approximately same as the length of the constant diameter (Dc) portion from the intermediate portion to the top portion,
   a tip portion (15) formed at an opened semi-circular shape to overlap the syringe over the syringe mounting device for snapping in, so that the smaller diameter portion (Dtip) of the lower semi-cylindrical tube section creates a frictional fit to secure the syringe to avoid the syringe separating from the lower semi-cylindrical tube section,
   wherein the semi-circular shaped locking groove (14), which is disposed between the upper semi-cylindrical tube section (10) and the lower semi-cylindrical tube section (13) is for receiving a flange of the syringe fixedly so that the axial movement of the syringe is prevented, and
   a piston press unit (20) having a threaded rod (24), which is screw-coupled to the threaded hole (12), so that the piston press unit (20) is movable along the threaded hole (12), while the syringe piston is depressed with a constant pressure for injecting a precise amount of medicine to a patient body.

2. The apparatus for operating a syringe piston according to claim 1, wherein said piston press unit (20) further comprises a handle (21) with an anti-slip knob section (22) formed at an outer peripheral surface of handle (21) for turning the handle.

3. The apparatus for operating a syringe piston according to claim 2, wherein said handle (21) further comprises a polygonal section (23) formed at a lower end portion thereof, and figures are marked on the polygonal section (23) to accurately calibrate injecting the amount of the medicine.

\* \* \* \* \*